US010563055B2

(12) United States Patent
Gong et al.

(10) Patent No.: US 10,563,055 B2
(45) Date of Patent: Feb. 18, 2020

(54) CARPET COMPOSITIONS AND METHODS OF MAKING THE SAME

(71) Applicant: ExxonMobil Chemical Patents Inc., Baytown, TX (US)

(72) Inventors: Yanan Gong, Shanghai (CN); Saifudin M. Abubakar, Shanghai (CN); Lan Li, Shanghai (CN)

(73) Assignee: ExxonMobil Chemical Patents Inc., Baytown, TX (US)

( * ) Notice: Subject to any disclaimer, the term of this patent is extended or adjusted under 35 U.S.C. 154(b) by 0 days.

(21) Appl. No.: 15/787,172

(22) Filed: Oct. 18, 2017

(65) Prior Publication Data

US 2018/0171129 A1    Jun. 21, 2018

Related U.S. Application Data

(60) Provisional application No. 62/436,812, filed on Dec. 20, 2016.

(51) Int. Cl.

| *C08L 23/16* | (2006.01) |
| *C08L 23/12* | (2006.01) |
| *B32B 27/30* | (2006.01) |
| *D06N 7/00* | (2006.01) |
| *G01N 25/48* | (2006.01) |

(52) U.S. Cl.
CPC .............. *C08L 23/12* (2013.01); *B32B 27/30* (2013.01); *D06N 7/0071* (2013.01); *B32B 2307/51* (2013.01); *C08L 2205/025* (2013.01); *C08L 2207/10* (2013.01); *G01N 25/4866* (2013.01)

(58) Field of Classification Search
CPC .................. C08L 23/12; C08L 2207/10; C08L 2205/025; B32B 27/30; B32B 2307/51; D06N 7/0071; D06N 2201/042
See application file for complete search history.

(56) References Cited

U.S. PATENT DOCUMENTS

| 3,956,554 | A | 5/1976 | Abel et al. |
| 4,543,399 | A | 9/1985 | Jenkins, III et al. |
| 4,588,790 | A | 5/1986 | Jenkins, III et al. |
| 4,702,950 | A | 10/1987 | Slosberg et al. |
| 4,960,823 | A * | 10/1990 | Komatsu et al. ....... C08L 53/00 525/88 |
| 5,001,205 | A | 3/1991 | Hoel |
| 5,028,670 | A | 7/1991 | Chinh et al. |
| 5,047,462 | A | 9/1991 | Kehr et al. |
| 5,317,036 | A | 5/1994 | Brady, III et al. |
| 5,352,749 | A | 10/1994 | DeChellis et al. |
| 5,405,922 | A | 4/1995 | DeChellis et al. |
| 5,436,304 | A | 7/1995 | Griffin et al. |
| 5,453,471 | A | 9/1995 | Bernier et al. |
| 5,462,999 | A | 10/1995 | Griffin et al. |
| 5,539,056 | A | 7/1996 | Yang et al. |
| 5,596,052 | A | 1/1997 | Resconi et al. |
| 5,616,661 | A | 4/1997 | Eisinger et al. |
| 5,627,242 | A | 5/1997 | Jacobsen et al. |
| 5,665,818 | A | 9/1997 | Tilston et al. |
| 5,668,228 | A | 9/1997 | Chinh et al. |
| 5,677,375 | A | 10/1997 | Rifi et al. |
| 6,500,563 | B1 | 12/2002 | Datta et al. |
| 6,503,595 | B1 | 1/2003 | Kim et al. |
| 6,881,800 | B2 | 4/2005 | Friedersdorf |
| 7,014,886 | B2 | 3/2006 | Vey et al. |
| 7,105,603 | B2 * | 9/2006 | Dharmarajan et al. ................ C08L 53/00 525/191 |
| 7,294,681 | B2 | 11/2007 | Jiang et al. |
| 7,524,910 | B2 | 4/2009 | Jiang et al. |
| 7,741,397 | B2 | 6/2010 | Liang et al. |
| 9,062,169 | B2 * | 6/2015 | Gusain et al. ............. C08J 5/18 |
| 2004/0052952 | A1 | 3/2004 | Vey et al. |
| 2007/0095453 | A1 | 5/2007 | Brumbelow et al. |
| 2008/0213515 | A1 | 9/2008 | Vey et al. |
| 2008/0280093 | A1 | 11/2008 | Bieser et al. |
| 2010/0279033 | A1 | 11/2010 | Becker et al. |
| 2010/0285246 | A1 | 11/2010 | Becker et al. |
| 2011/0256335 | A1 | 10/2011 | Brumbelow et al. |
| 2014/0017439 | A1 | 1/2014 | Siskovich et al. |

FOREIGN PATENT DOCUMENTS

| EP | 0 518 014 A | 12/1992 |
| EP | 0 570 236 A | 11/1993 |
| EP | 0 634 421 A | 1/1995 |
| EP | 0 794 200 A | 9/1997 |
| EP | 0 802 202 A | 10/1997 |
| JP | 05132870 A | 5/1993 |
| WO | 96/33227 A | 10/1996 |
| WO | 97/22639 A | 6/1997 |
| WO | 99/40160 A | 8/1999 |
| WO | 2005/052246 A | 6/2005 |
| WO | 2008/027125 A | 3/2008 |
| WO | 2008/124449 A | 10/2008 |
| WO | 2009/086251 A | 7/2009 |
| WO | 2010/075251 A | 7/2010 |
| WO | 2013/134038 A | 9/2013 |
| WO | 2015/002747 A | 1/2015 |

* cited by examiner

Primary Examiner — Nathan M Nutter (57) ABSTRACT

This invention relates to carpet backing layer compositions including a blend of polyolefins (e.g., propylene-based elastomers) which have enhanced flexibility and good processability. Carpets including such backing layer compositions and methods of making such carpets are also provided.

25 Claims, 2 Drawing Sheets

CARPET COMPOSITIONS AND METHODS OF MAKING THE SAME

PRIORITY CLAIM

This applications claims priority to and the benefit of U.S. Ser. No. 62/436,812, filed Dec. 20, 2016 and is incorporated by reference in its entirety.

FIELD OF THE INVENTION

This invention relates to compositions that can be used in carpet backing, in particular to compositions comprising a blend of propylene-based elastomers. The present disclosure also relates to carpets comprising such compositions and methods of making such carpets.

BACKGROUND OF THE INVENTION

Most conventional carpets comprise a primary backing layer with fiber tufts in the form of cut or uncut loops extending upwardly from the backing to form a pile surface. For example, one type of carpeting includes decorative three-dimensional (3D) carpet where 3D woven microfiber polyester may be attached to a backing layer. Important features for carpet backing layers include flexibility, ease of processability, low volatile organic compound (VOC) emissions as well as a good visual aesthetic.

Some conventional backing layers comprise rubber materials, such as nitrile butadiene rubber and styrene-butadiene rubber, to achieve the appropriate flexibility. However, these rubber materials can have undesirably high VOC emissions as well as increased processing time due to the need for extending curing times to form the carpet. Furthermore, such rubber materials are usually a black color, which can be aesthetically unattractive to a consumer. While polyolefins may be considered to be a desirable alternative for the backing layers since they can produce a transparent backing layer with high clarity and low VOC emissions, such backing layers comprising polyolefins can be too rigid to provide the required flexibility. Thus, there is a need for backing layer compositions which not only have the required flexibility, low VOC emission and good processability, but also are transparent for improved aesthetics.

SUMMARY OF THE INVENTION

Despite known difficulties in using polyolefins in backing layer compositions, it has been unexpectedly found that various blends of polyolefins (e.g., polypropylene-based elastomers) can achieve the required flexibility, low VOC emissions, good processability and transparency.

Thus, this invention relates to a carpet backing layer comprising one of the following:

(i) a first blend comprising:
 (A) about 30 wt % to about 50 wt % of a first propylene-based elastomer comprising at least about 90 wt % propylene-derived units and about 2 to about 10 wt % ethylene-derived units, by weight of the propylene-based elastomer, wherein the first propylene-based elastomer has a 1% secant flexural modulus of about 350 MPa to about 450 MPa;
 (B) about 5.0 wt % to about 20 wt % of a second propylene-based elastomer comprising at least about 80 wt % propylene-derived units and about 5 to about 20 wt % ethylene-derived units, by weight of the propylene-based elastomer, wherein the second propylene-based elastomer has a 1% secant flexural modulus of about 40 MPa to about 70 MPa;
 (C) about 35 wt % to about 60 wt % of a third propylene-based elastomer comprising at least about 75 wt % propylene-derived units and about 10 to about 25 wt % ethylene-derived units, by weight of the propylene-based elastomer, wherein the third propylene-based elastomer has a 1% secant flexural modulus of about 5.0 MPa to about 20 MPa; and
 (D) about 1.0 wt % to about 10 wt % of a fourth propylene-based elastomer comprising at least about 90 wt % propylene-derived units and about 2 to about 10 wt % ethylene-derived units, by weight of the propylene-based elastomer, wherein the fourth propylene-based elastomer has a melt mass-flow rate of at least about 20,000 g/10 min;
(ii) a second blend comprising:
 about 5.0 wt % to about 20 wt % of the first propylene-based elastomer;
 about 10 wt % to about 30 wt % of the second propylene-based elastomer;
 about 55 wt % to about 75 wt % of the third propylene-based elastomer; and
 about 1 wt % to about 10 wt % of the fourth propylene-based elastomer; or
(iii) a third blend comprising:
 about 80 wt % to about 98 wt % of the second propylene-based elastomer; and
 about 2.0 wt % to about 20 wt % of the fourth propylene-based elastomer.

In another aspect, this disclosure relates to a carpet comprising a backing layer as described herein and a plurality of fibers attached to the backing layer.

In yet another aspect, this disclosure relates to a method for making a carpet comprising: attaching a backing layer as described herein to a plurality of fibers via hot compression for a period of time of less than about 10 minutes to form the carpet.

BRIEF DESCRIPTION OF THE FIGURES

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION OF THE INVENTION

I. Definitions

To facilitate an understanding of the present invention, a number of terms and phrases are defined below.

As used in the present disclosure and claims, the singular forms "a," "an," and "the" include plural forms unless the context clearly dictates otherwise.

The term "and/or" as used in a phrase such as "A and/or B" herein is intended to include "A and B", "A or B", "A", and "B".

As used herein, a "polymer" may be used to refer to homopolymers, copolymers, interpolymers, terpolymers, etc.

As used herein, when a polymer is referred to as comprising a monomer, the monomer is present in the polymer in the polymerized form of the monomer or in the derivative form of the monomer.

As used herein, when a polymer composition or blend is said to comprise a certain percentage, wt %, of a monomer, that percentage of monomer is based on the total amount of monomer units of all the polymer components of the polymer composition or blend.

As used herein, "elastomer" or "elastomeric composition" refers to any polymer or composition of polymers (such as blends of polymers) consistent with the ASTM D1566 definition. Elastomer includes mixed blends of polymers such as melt mixing and/or reactor blends of polymers. The terms may be used interchangeably with the term "rubber(s)."

A "polyolefin" is a polymer comprising at least 50 wt % of one or more olefin monomers. Preferably, a polyolefin comprises at least 60 wt %, or at least 70 wt %, or at least is 80 wt %, or at least 90 wt %, or at least 95 wt %, or 100 w %, of one or more olefin monomers.

Preferably, a polyolefin comprises 1-olefins, having carbon numbers of 2 to 20, or 2 to 16, or 2 to 10, or 2 to 8, or 2 to 6.

As used herein, when a layer is referred to as "substantially" locking the plurality of fibers extending from the backing layer in, it means that at least about 90%, at least about 92%, at least about 94%, at least about 96%, or at least about 98% of the fibers are held in place after being rolled over by a Velcro type tool for about 20 times in a Velcro roller test. Preferably, no fuzzing is visible to the naked eye.

As used herein, "carpet" also includes carpet tiles and portions of a carpet.

II. Carpeting

This disclosure relates to carpet compositions including backing layers comprising various blends of polyolefins (e.g., propylene-based elastomers). While use of polyolefins in carpeting backing layers can be problematic because of the lack of flexibility of the resultant backing layer, it was surprisingly found that blends of polyolefins (e.g., propylene-based elastomers) described herein can achieve the required flexibility, low VOC emissions, good processability as well as the required transparency.

In various embodiments, carpets and carpet backing layers comprising blends of propylene-based elastomers are provided.

A. Propylene-Based Elastomers

The propylene-based elastomers may be a copolymer of propylene-derived units and units derived from at least one of ethylene or a $C_{4-10}$ alpha-olefin. The propylene-based elastomer may contain at least about 60 wt % propylene-derived units based on the weight of the propylene-based elastomer. The propylene-based elastomer may have limited crystallinity due to adjacent isotactic propylene units and a melting point as described herein. The crystallinity and the melting point of the propylene-based elastomer can be reduced compared to highly isotactic polypropylene by the introduction of errors in the insertion of propylene. The propylene-based elastomer is generally devoid of any substantial intermolecular heterogeneity in tacticity and comonomer composition, and also generally devoid of any substantial heterogeneity in intramolecular composition distribution.

The amount of propylene-derived units present in the propylene-based elastomer may be present in an amount from at least about 60 wt %, at least about 65 wt %, at least about 70 wt %, at least about 75 wt %, at least about 80 wt %, at least about 84 wt %, at least about 85 wt %, at least about 88 wt %, at least about 90 wt %, at least about 92 wt %, at least about 94 wt %, at least about 96 wt % or at least about 98 wt % of the propylene-based elastomer. Additionally or alternatively, the amount of propylene-derived units present in the propylene-based elastomer may be present in an amount of, at most about 98 wt %, at most about 96 wt %, at most about 94 wt %, at most about 92 wt %, at most about 90 wt %, at most about 88 wt %, at most abut 85 wt %, at most about 84 wt % or at most about 80 wt % of the propylene-based elastomer. Ranges expressly disclosed include combinations of any of the above-enumerated values; e.g., about 60 to about 98 wt %, about 70 to about 98 wt %, about 80 to about 98 wt %, about 85 to about 98 wt %, about 90 to about 98 wt %, about 70 to about 96 wt %, about 75 to about 96 wt %, about 80 to 96 wt %, about 85 to about 96 wt %, about 90 to about 96 wt %, etc.

The units, or comonomers, derived from at least one of ethylene or a $C_{4-10}$ alpha-olefin may be present in an amount of about 1 to about 35 wt %, or about 2 to about 35 wt %, or about 5 to about 35 wt %, or about 7 to about 32 wt %, or about 8 to about 25 wt %, or about 10 to about 25 wt %, or about 12 to about 20 wt %, or about 8 to about 20 wt %, or about 8 to about 18 wt %, or about 5 to about 20 wt %, or about 5 to about 15 wt %, or about 2 to about 10 wt %, or about 2 to about 6.0 wt %, based on the weight of the propylene-based elastomer.

In preferred embodiments, the comonomer is ethylene, 1-hexene, or 1-octene. In some embodiments, the propylene-based elastomer comprises ethylene-derived units or consists essentially of units derived from propylene and ethylene, i.e., the propylene-based elastomer does not contain any other comonomer in an amount other than that typically present as impurities in the ethylene and/or propylene feedstreams used during polymerization, or in an amount that would materially affect the 1% secant flexural modulus and/or melt mass-flow rate of the propylene-based elastomer, or any other comonomer intentionally added to the polymerization process. In such embodiments, the propylene-based elastomer may comprise about 2 to about 25 wt %, or about 5 to about 25 wt %, or about 10 to about 25 wt %, or about 6 to about 22 wt %, or about 12 to about 20 wt %, or about 7 to about 20 wt %, or about 5 to about 20 wt %, or about 5 to about 15 wt %, or about 8 to about 17 wt %, or about 9 to 16 wt %, or about 2 to about 10 wt % or about 2 to about 6.0 wt %, ethylene-derived units based on the weight of the propylene-based elastomer.

The propylene-based elastomer may comprise more than one comonomer. Preferred embodiments of a propylene-based elastomer having more than one comonomer include propylene-ethylene-octene, propylene-ethylene-hexene, and propylene-ethylene-butene polymers. In embodiments where more than one comonomer derived from at least one of ethylene or a $C_{4-10}$ alpha-olefin is present, the amount of one comonomer may be less than about 5 wt % of the propylene-based elastomer, but the combined amount of comonomers of the propylene-based elastomer is about 5 wt % or greater.

In some embodiments, the propylene-based elastomer may further comprise a diene. The optional diene may be any hydrocarbon structure having at least two unsaturated bonds wherein at least one of the unsaturated bonds is readily incorporated into a polymer. For example, the optional diene may be selected from straight chain acyclic olefins, such as 1,4-hexadiene and 1,6-octadiene; branched chain acyclic olefins, such as 5-methyl-1,4-hexadiene, 3,7-dimethyl-1,6-octadiene, and 3,7-dimethyl-1,7-octadiene; single ring alicyclic olefins, such as 1,4-cyclohexadiene, 1,5-cyclooctadiene, and 1,7-cyclododecadiene; multi-ring alicyclic fused and bridged ring olefins, such as tetrahydroindene, norbornadiene, methyl-tetrahydroindene, dicyclopentadiene, bicyclo-(2.2.1)-hepta-2,5-diene, norbornadiene, alkenyl norbornenes, alkylidene norbornenes, e.g., ethylidiene norbornene ("ENB"), cycloalkenyl norbornenes, and cycloalkyliene norbornenes (such as 5-methylene-2-norbornene, 5-ethylidene-2-norbornene, 5-propenyl-2-norbornene, 5-isopropylidene-2-norbornene, 5-(4-cyclopentenyl)-2-norbornene, 5-cyclohexylidene-2-norbornene, 5-vinyl-2-norbornene); and cycloalkenyl-substituted alkenes, such as vinyl cyclohexene, allyl cyclohexene, vinyl cyclooctene, 4-vinyl cyclohexene, allyl cyclodecene, vinyl cyclododecene, and tetracyclo (A-11,12)-5,8-dodecene. The amount of diene-derived units present in the propylene-based elastomer may range from an upper limit of about 15%, about 10%, about 7%, about 5%, about 4.5%, about 3%, about 2.5%, or about 1.5%, to a lower limit of about 0%, about 0.1%, about 0.2%, about 0.3%, about 0.5%, or about 1%, based on the total weight of the propylene-based elastomer. In some embodiments, the propylene-based elastomer does not contain any diene-derived units.

The propylene-based elastomer may have a triad tacticity of three propylene units, as measured by 13C NMR, of at least about 75%, at least about 80%, at least about 82%, at least about 85%, or at least about 90%. Preferably, the propylene-based elastomer has a triad tacticity of about 50 to about 99%, about 60 to about 99%, about 75 to about 99%, or about 80 to about 99%. In some embodiments, the propylene-based elastomer may have a triad tacticity of about 60 to 97%.

The propylene-based elastomer may have a heat of fusion ("Hf"), as determined by DSC as described herein, of about 75 J/g or less, about 70 J/g or less, about 50 J/g or less, or about 45 J/g or less, or about 35 J/g or less. The propylene-based elastomer may have a lower limit Hf of about 0.5 J/g, about 1 J/g, or about 5 J/g. For example, the Hf value may be anywhere from 1.0, 1.5, 3.0, 4.0, 6.0, or 7.0 J/g, to 30, 35, 40, 50, 60, 70, or 75 J/g.

The propylene-based elastomer may have a percent crystallinity, as determined according to the DSC procedure described herein, of about 2 to about 65%, about 0.5 to about 40%, about 1 to about 30%, or about 5 to about 35%, of the crystallinity of isotactic polypropylene. The thermal energy for the highest order of propylene (i.e., 100% crystallinity) is estimated at 189 J/g. In some embodiments, the copolymer has crystallinity less than 40%, or in the range of about 0.25 to about 25%, or about 0.5 to about 22%, of isotactic polypropylene. Embodiments of the propylene-based elastomer may have a tacticity index m/r from a lower limit of about 4 or about 6 to an upper limit of about 8 or about 10 or about 12. In some embodiments, the propylene-based elastomer has an isotacticity index greater than 0%, or within the range having an upper limit of about 50% or about 25%, and a lower limit of about 3% or about 10%.

The propylene-based elastomer may have a 1% secant flexural modulus, as measured according to ASTM D790, of at least about 5.0 MPa, at least about 10 MPa, at least about 20 MPa, at least about 30 MPa, at least about 40 MPa, at least about 50 MPa, at least about 60 MPa, at least about 70 MPa, at least about 80 MPa, at least about 90 MPa, at least about 100 MPa, at least about 125 MPa, at least about 150 MPa, at least about 175 MPa, at least about 200 MPa, at least about 225 MPa, at least about 250 MPa, at least about 275 MPa, at least about 300 MPa, at least about 325 MPa, at least about 350 MPa, at least about 375 MPa, at least about 400 MPa, at least about 425 MPa, at least about 450 MPa, at least about 475 MPa, or about 500 MPa. Additionally or alternatively, the propylene-based elastomer may have a 1% secant flexural modulus, as measured according to ASTM D790, of at most about 500 MPa, at most about 475 MPa, at most about 450 MPa, at most about 425 MPa, at most about 400 MPa, at most about 375 MPa, at most about 350 MPa, at most about 325 MPa, at most about 300 MPa, at most about 275 MPa, at most about 250 MPa, at most about 225 MPa, at most about 200 MPa, at most about 175 MPa, at most about 150 MPa, at most about 125 MPa, at most about 100 MPa, at most about 90 MPa, at most about 80 MPa, at most about 70 MPa, at most about 60 MPa, at most about 50 MPa, at most about 40 MPa, at most about 30 MPa, at most about 20 MPa, at most about 10 MPa, or about 5.0 MPa. Ranges expressly disclosed include combinations of any of the above-enumerated values; e.g., about 5.0 to about 500 MPa, about 5.0 to 250 MPa, about 5.0 to about 100 MPa, about 5.0 to about 50 MPa, about 5 to about 20 MPa, about 20 to about 500 MPa, about 20 to 250 MPa, about 20 to about 100 MPa, about 20 to about 50 MPa, about 40 to about 500 MPa, about 40 to 250 MPa, about 40 to about 100 MPa, about 40 to about 70 MPa, about 40 to about 60 MPa, about 50 to about 500 MPa, about 50 to about 250 MPa, about 50 to about 100 MPa, about 100 to about 500 MPa, about 100 to about 250 MPa, about 200 to about 500 MPa, about 200 to about 450 MPa, about 200 to about 400 MPa, about 200 to about 350 MPa, about 200 to about 300 MPa, about 300 to about 500 MPa, about 300 to about 450 MPa, about 300 to about 400 MPa, about 300 to about 350 MPa, about 350 to about 500 MPa, about 350 to about 450 MPa, about 350 to about 400 MPa, etc.

The propylene-based elastomer may have a melt mass-flow rate, as measured according to ASTM D1238, 2.16 kg at 230° C., of at least about 5 g/10 min, at least about 15 g/10 min, at least about 50 g/10 min, at least about 100 g/10 min, at least about 1,000 g/10 min, at least about 2,500 g/10 min, at least about 5,000 g/10 min, at least about 7,500 g/10 min, at least about 10,000 g/10 min, at least about 12,500 g/10 min, at least about 15,000 g/10 min, at least about 17,500 g/10 min, at least about 20,000 g/10 min, at least about 22,500 g/10 min, at least about 25,000 g/10 min, at least about 27,500 g/10 min or about 30,000 g/10 min. Additionally or alternatively, the propylene-based elastomer may have a melt mass-flow rate, as measured according to ASTM D1238, 2.16 kg at 230° C., of at most about 30,000 g/10 min, at most about 27,500 g/10 min, at most about 25,000 g/10 min, at most about 22,500 g/10 min, at most about 20,000 g/10 min, at most about 17,500 g/10 min, at most about 15,000 g/10 min, at most about 12,500 g/10 min, at most about 10,000 g/10 min, at most about 7,500 g/10 min, at most about 5,000 g/10 min, at most about 2,500 g/10 min, at most about 1,000 g/10 min, at most about 100 g/10 min, at most about 50 g/10 min, at most about 15 g/10 min, or about 5 g/10 min. Ranges expressly disclosed include combinations of any of the above-enumerated values; e.g., about 5 to about 30,000 g/10 min, about 5 to about 20,000 g/10 min, about 5 to about 10,000 g/10 min, about 5 to about 1,000 g/10 min, about 5 to about 100 g/10 min, about 5 to about 50 g/10 min, about 5 to about 15 g/10 min, about 1,000 to about 30,000 g/10 min, about 1,000 to about 20,000 g/10 min, about 1,000 to about 10,000 g/10 min, about 1,000 to about 5,000 g/10 min, about 10,000 to about 30,000 g/10 min, about 10,000 to about 20,000 g/10 min, about 10,000 to about 15,000 g/10 min, about 20,000 to about 30,000 g/10 min, about 20,000 to about 27,500 g/10 min, about 22,500 to about 30,000 g/10 min, about 22,500 to about 27,500,000 g/10 min, about 22,500 to about 25,000 g/10 min, etc. The propylene-based elastomer may have a $T_m$ of about 105° C. or less, about 100° C. or less, about 90° C. or less, about 80° C. or less, or about 70° C. or less. In some embodiments, the propylene-based elastomer has a $T_m$ of about 25 to about 105° C., about 60 to about 105° C., about 70 to about 105° C., or about 90 to about 105° C.

The DSC procedures for determining $T_m$ and Hf of the PBE include the following. The polymer is pressed at a temperature of from 200° C. to 230° C. in a heated press, and the resulting polymer sheet is hung, under ambient conditions (of 20-23.5° C.), in the air to cool. 6 to 10 mg of the polymer sheet is removed with a punch die. This 6 to 10 mg sample is annealed at room temperature (22° C.) for 80 to 100 hours. At the end of this period, the sample is placed in a DSC (Perkin Elmer Pyris One Thermal Analysis System) and cooled at a rate of about 10° C./min to −30° C. to −50° C. and held for 10 minutes at −50° C. The sample is heated at 10° C./min to attain a final temperature of 200° C. The sample is kept at 200° C. for 5 minutes. Then a second cool-heat cycle is performed, using the same conditions described above. Events from both cycles, "first melt" and "second melt", respectively, are recorded. The thermal output is recorded as the area under the melting peak of the sample, which typically occurs between 0° C. and 200° C. It is measured in Joules and is a measure of the Hf of the polymer. Reference to melting point temperature and Hf herein refers to the first melt.

The propylene-based elastomer may have a density of about 0.850 to about 0.920 g/cm³, or about 0.860 to about 0.890 g/cm³, at room temperature as measured per ASTM D1505.

The propylene-based elastomer may have a melt index (MI), as measured per ASTM D1238, 2.16 kg at 190° C., of at least about 1.0 g/10 min, at least about 1.5 g/10 min, at least about 2.0 g/10 min, at least about 2.5 g/10 min, at least about 3.0 g/10 min, at least about 5 g/10 min, at least about 10.0 g/10 min, or about 15.0 g/10 min.

The propylene-based elastomer may have an elongation at break, as measured per ASTM D638 of at least about 200%, at least about 500%, at least about 1000%, at least about 1500%, at least about 2000% or at least about 3000%.

The propylene-based elastomer may have a weight average molecular weight (Mw) of about 5,000 to about 5,000,000 g/mole, about 10,000 to about 1,000,000 g/mole, about 20,000 to about 750,000 g/mole, about 30,000 to about 400,000 g/mole.

The propylene-based elastomer may have a number average molecular weight (Mn) of about 2,500 to about 250,000 g/mole, about 10,000 to about 250,000 g/mole, or about 25,000 to about 200,000 g/mole.

The propylene-based elastomer may have a z-average molecular weight (Mz) of about 10,000 to about 7,000,000 g/mole, about 80,000 to about 700,000 g/mole, or about 100,000 to about 500,000 g/mole.

The propylene-based elastomer may have a molecular weight distribution ("MWD") of about 1.5 to about 20, or about 1.5 to about 15, preferably about 1.5 to about 5, and more preferably about 1.8 to about 3, and most preferably about 1.8 to about 2.5.

Molecular weight (weight-average molecular weight, $M_w$, number-average molecular weight, $M_n$, and molecular weight distribution, $M_w/M_n$ or MWD) were determined using a High Temperature Size Exclusion Chromatograph (either from Waters Corporation or Polymer Laboratories), equipped with a differential refractive index detector (DRI), an online light scattering (LS) detector, and a viscometer.

Three Polymer Laboratories PLgel 10 mm Mixed-B columns were used. The nominal flow rate was 0.5 cm³/min, and the nominal injection volume was 300 μL. The various transfer lines, columns and differential refractometer (the DRI detector) were contained in an oven maintained at 145° C. Polystyrene was used to calibrate the instrument.

Solvent for the SEC experiment is prepared by dissolving 6 g of butylated hydroxy toluene as an antioxidant in 4 L of Aldrich reagent grade 1,2,4 trichlorobenzene (TCB). The TCB mixture is then filtered through a 0.7 μm glass pre-filter and subsequently through a 0.1 μm Teflon filter. The TCB is then degassed with an online degasser before entering the SEC. Polymer solutions are prepared by placing the dry polymer in a glass container, adding the desired amount of TCB, then heating the mixture at 160° C. with continuous agitation for about 2 hr. All quantities are measured gravimetrically. The TCB densities used to express the polymer concentration in mass/volume units are 1.463 g/mL at room temperature and 1.324 g/mL at 135° C. The injection concentration ranges from 1.0 to 2.0 mg/mL, with lower concentrations being used for higher molecular weight samples. Prior to running each sample the DRI detector and the injector are purged. Flow rate in the apparatus is then increased to 0.5 mL/min, and the DRI was allowed to stabilize for 8-9 hr before injecting the first sample. The LS laser is turned on 1 to 1.5 hr before running samples.

The concentration, c, at each point in the chromatogram is calculated from the baseline-subtracted DRI signal, $I_{DRI}$, using the following equation:

$$c = K_{DRI} I_{DRI}/(dn/dc)$$

where $K_{DRI}$ is a constant determined by calibrating the DRI, and dn/dc is the same as described below for the LS analysis. Units on parameters throughout this description of the SEC method are such that concentration is expressed in g/cm³, molecular weight is expressed in kg/mol, and intrinsic viscosity is expressed in dL/g.

The light scattering detector used is a Wyatt Technology High Temperature mini-DAWN. The polymer molecular weight, M, at each point in the chromatogram is determined by analyzing the LS output using the Zimm model for static light scattering (M. B. Huglin, Light Scattering from Polymer Solutions, Academic Press, 1971):

$$[K_o c/\Delta R(\theta,c)] = [1/MP(\theta)] + 2A_2 c$$

where $\Delta R(\theta)$ is the measured excess Rayleigh scattering intensity at scattering angle θ, c is the polymer concentration determined from the DRI analysis, $A_2$ is the second virial coefficient, $P(\theta)$ is the form factor for a monodisperse random coil (described in the above reference), and $K_o$ is the optical constant for the system:

$$K_o = \frac{4\pi^2 n^2 (dn/dc)^2}{\lambda^4 N_A},$$

in which $N_A$ is the Avogadro's number, and dn/dc is the refractive index increment for the system. The refractive index, n=1.500 for TCB at 135° C. and λ=690 nm. In addition, $A_2$=0.0015 and dn/dc=0.104 for ethylene polymers, whereas $A_2$=0.0006 and dn/dc=0.104 for propylene polymers.

The molecular weight averages are usually defined by considering the discontinuous nature of the distribution in which the macromolecules exist in discrete fractions i containing $N_i$ molecules of molecular weight $M_i$. The weight-average molecular weight, $M_w$, is defined as the sum of the products of the molecular weight $M_i$ of each fraction multiplied by its weight fraction $w_i$:

$$M_w = \Sigma w_i M_i = (\Sigma N_i M_i^2 / \Sigma N_i M_i),$$

since the weight fraction $w_i$ is defined as the weight of molecules of molecular weight $M_i$ divided by the total weight of all the molecules present:

$$w_i = N_i M_i / \Sigma N_i M_i,$$

The number-average molecular weight, $M_n$, is defined as the sum of the products of the molecular weight $M_i$ of each fraction multiplied by its mole fraction $x_i$:

$$M_n = \Sigma x_i M_i = \Sigma N_i M_i / \Sigma N_i,$$

since the mole fraction $x_i$ is defined as $N_i$ divided by the total number of molecules:

$$x_i = N_i / \Sigma N_i.$$

In the SEC, a high temperature Viscotek Corporation viscometer is used, which has four capillaries arranged in a Wheatstone Bridge configuration with two pressure transducers. One transducer measures the total pressure drop across the detector, and the other, positioned between the two sides of the bridge, measures a differential pressure. The specific viscosity, $\eta_s$, for the solution flowing through the viscometer is calculated from their outputs. The intrinsic viscosity, [η], at each point in the chromatogram is calculated from the following equation:

$$\eta_s = c[\eta] + 0.3(c[\eta])^2,$$

where c was determined from the DRI output.

The branching index (g', also referred to as g'(vis)) is calculated using the output of the SEC-DRI-LS-VIS method as follows. The average intrinsic viscosity, $[\eta]_{avg}$, of the sample is calculated by:

$$[\eta]_{avg} = \frac{\Sigma c_i [\eta]_i}{\Sigma c_i},$$

where the summations are over the chromatographic slices, i, between the integration limits.

Various propylene-based elastomers having any combination of the above-described properties are contemplated herein.

The propylene-based elastomer may comprise copolymers prepared according to the procedures described in WO 02/36651, U.S. Pat. No. 6,992,158, and/or WO 00/01745, the contents of which are incorporated herein by reference. Preferred methods for producing the propylene-based elastomer may be found in U.S. Pat. Nos. 7,232,871 and 6,881,800, the contents of which are incorporated herein by reference. The invention is not limited by any particular polymerization method for preparing the propylene-based elastomer, and the polymerization processes are not limited by any particular type of reaction vessel.

Suitable propylene-based elastomers may be available commercially under the trade names VISTAMAXX™ (ExxonMobil Chemical Company, Tex., USA) (e.g., VISTAMAXX™ 3000, VISTAMAXX™ 3588FL, VISTAMAXX™ 6102, VISTAMAXX™ 8880), VERSIFY™ (The Dow Chemical Company, Mich., USA), certain grades of TAFMER™ XM or NOTIO™ (Mitsui Company, Japan), and certain grades of SOFTEL™ (Basell Polyolefins of the Netherlands). The particular grade(s) of commercially available propylene-based elastomer suitable for use in the invention can be readily determined using methods commonly known in the art.

B. Carpet Backing Layer

In various embodiments, blends of the propylene-based elastomers described herein having combinations of the above-described properties for use in carpet backing layer compositions are provide herein. Such carpet backing layer compositions may advantageously have good flexibility, processability and transparency. In particular, blends comprising a first propylene-based elastomer, a second propylene-based elastomer, a third propylene-based elastomer, and/or a fourth propylene-based elastomer, each having combinations of the above-described properties, are contemplated herein.

The first propylene-based elastomer may comprise propylene-derived units and ethylene-derived units in amounts as described above, particularly, at least about 90 wt % or at least about 94 wt % propylene-derived units; and about 2 to about 10 wt % or about 2 to about 6.0 wt % ethylene-derived units, by weight of the propylene-based elastomer. Additionally, the first propylene-based elastomer may have a 1% secant flexural modulus, as measured according to ASTM D790, as described above, particularly, about 350 MPa to about 450 MPa or about 350 MPa to about 400 MPa.

The second propylene-based elastomer may comprise propylene-derived units and ethylene-derived units in amounts as described above, particularly, at least about 80 wt % or at least about 85 wt % propylene-derived units; and about 5 to about 20 wt % or about 5 to about 15 wt % ethylene-derived units, by weight of the propylene-based elastomer. Additionally, the second propylene-based elastomer may have a 1% secant flexural modulus, as measured according to ASTM D790, as described above, particularly, about 40 MPa to about 70 MPa or about 40 MPa to about 70 MPa.

The third propylene-based elastomer may comprise propylene-derived units and ethylene-derived units in amounts as described above, particularly, at least about 75 wt % or at least about 80 wt % propylene-derived units; and about 10 to about 25 wt % or about 12 to about 20 wt % ethylene-derived units, by weight of the propylene-based elastomer. Additionally, the third propylene-based elastomer may have a 1% secant flexural modulus, as measured according to ASTM D790, as described above, particularly, about 5.0 MPa to about 20 MPa or about 10 MPa to about 20 MPa.

The fourth propylene-based elastomer may comprise propylene-derived units and ethylene-derived units in amounts as described above, particularly, at least about 80 wt % or at least about 85 wt % propylene-derived units; and about 5 to about 20 wt % or about 5 to about 15 wt % ethylene-derived units, by weight of the propylene-based elastomer. Additionally, the fourth propylene-based elastomer may have a 1% secant flexural modulus, as measured according to ASTM D790, as described above, particularly, about 5.0 MPa to about 20 MPa or about 10 MPa to about 20 MPa.

1. First Blend

In various embodiments, a first blend comprising the first, second, third and fourth propylene-based elastomers as described herein are provided. The first propylene-based elastomer may be present in the first blend in an amount based on the total blend of at least about 25 wt %, at least about 30 wt %, at least about 35 wt %, at least about 40 wt %, at least about 45 wt %, at least about 50 wt % or at least about 55 wt %. Additionally or alternatively, the first propylene-based elastomer may be present in the first blend in an amount based on the total blend of about 25 to about 55 wt %, about 30 to about 55 wt %, about 30 to about 50 wt %, about 35 to about 45 wt %, about 30 to about 40 wt %, or about 35 to about 40 wt %, particularly, about 30 to about 50 wt % or about 35 to about 45 wt %.

The second propylene-based elastomer may be present in the first blend in an amount based on the total blend of at least about 5 wt %, at least about 10 wt %, at least about 15 wt %, at least about 20 wt %, or at least about 25 wt %. Additionally or alternatively, the second propylene-based elastomer may be present in the first blend in an amount based on the total blend of about 5 to about 25 wt %, about 5 to about 20 wt %, about 5 to about 15 wt %, or about 5 to 10 wt %, particularly, about 5 to about 20 wt % or about 5 to about 15 wt %.

The third propylene-based elastomer may be present in the first blend in an amount based on the total blend of at least about 35 wt %, at least about 40 wt %, at least about 45 wt %, at least about 50 wt %, at least about 55 wt %, at least about 60 wt %, or at least about 65 wt %. Additionally or alternatively, the third propylene-based elastomer may be present in the first blend in an amount based on the total blend of about 35 to about 65 wt %, about 35 to about 60 wt %, about 40 to about 60 wt %, about 40 to about 55 wt %, or about 45 to about 50 wt %, particularly, about 35 to about 60 wt % or about 40 to about 55 wt %.

The fourth propylene-based elastomer may be present in the first blend in an amount based on the total blend of at least about 1.0 wt %, at least about 2.0 wt %, at least about 4.0 wt %, at least about 5.0 wt %, at least about 7.0 wt %, or at least about 10 wt %. Additionally or alternatively, the fourth propylene-based elastomer may be present in the first blend in an amount based on the total blend of about 1.0 to about 10 wt %, about 1.0 to about 7.0 wt %, about 2.0 to about 7.0 wt %, or about 4.0 to about 7.0 wt %, particularly, about 1.0 to about 10 wt % or about 2.0 to about 7.0 wt %.

In a particular embodiment, a carpet backing layer is provided comprising a first blend as described herein. The first blend may comprise: the first propylene-based elastomer in an amount based on the total blend of about 30 to about 50 wt % or about 35 to 45 wt %; the second propylene-based elastomer in an amount based on the total blend of about 5.0 to about 20 wt % or about 5.0 to 15 wt %; the third propylene-based elastomer in an amount based on the total blend of about 35 to about 60 wt % or about 40 to about 55 wt %; and the fourth propylene-based elastomer in an amount based on the total blend of about 1.0 to about 10 wt % or about 2.0 to about 7.0 wt %.

2. Second Blend

In various embodiments, a second blend comprising the first, second, third and fourth propylene-based elastomers as described herein are provided. The first propylene-based elastomer may be present in the second blend in an amount based on the total blend of at least about 5.0 wt %, at least about 8.0 wt %, at least about 10 wt %, at least about 15 wt %, at least about 18 wt %, at least about 20 wt %, or at least about 25 wt %. Additionally or alternatively, the first propylene-based elastomer may be present in the first blend in an amount based on the total blend of about 5.0 to about 25 wt %, about 5.0 to about 20 wt %, about 8.0 to about 18 wt %, or about 10 to about 15 wt %, particularly, about 5.0 to about 20 wt % or about 8.0 to about 18 wt %.

The second propylene-based elastomer may be present in the second blend in an amount based on the total blend of at least about 10 wt %, at least about 12 wt %, at least about 15 wt %, at least about 18 wt %, at least about 20 wt %, at least about 22 wt %, at least about 25 wt %, at least about 30 wt % or at least about 35 wt %. Additionally or alternatively, the second propylene-based elastomer may be present in the second blend in an amount based on the total blend of about 10 to about 35 wt %, about 10 to about 30 wt %, about 12 to about 25 wt %, about 12 to about 22 wt %, or about 15 to about 20 wt %, particularly, about 10 to about 30 wt % or about 12 to about 22 wt %.

The third propylene-based elastomer may be present in the second blend in an amount based on the total blend of at least about 50 wt %, at least about 55 wt %, at least about 60 wt %, at least about 65 wt %, at least about 70 wt %, at least about 75 wt % or at least about 80 wt %. Additionally or alternatively, the third propylene-based elastomer may be present in the second blend in an amount based on the total blend of about 50 to about 80 wt %, about 50 to about 75 wt %, about 55 to about 75 wt %, about 60 to about 70 wt %, or about 60 to about 65 wt %, particularly, about 55 to about 75 wt % or about 60 to about 70 wt %.

The fourth propylene-based elastomer may be present in the second blend in an amount based on the total blend of at least about 1.0 wt %, at least about 2.0 wt %, at least about 4.0 wt %, at least about 5.0 wt %, at least about 7.0 wt %, or at least about 10 wt %. Additionally or alternatively, the fourth propylene-based elastomer may be present in the second blend in an amount based on the total blend of about 1.0 to about 10 wt %, about 1.0 to about 7.0 wt %, about 2.0 to about 7.0 wt %, or about 4.0 to about 7.0 wt %, particularly, about 1.0 to about 10 wt % or about 2.0 to about 7.0 wt %.

In a particular embodiment, a carpet backing layer is provided comprising a second blend as described herein. The second blend may comprise: the first propylene-based elastomer in an amount based on the total blend of about 5.0 to about 20 wt % or about 8.0 to 18 wt %; the second propylene-based elastomer in an amount based on the total blend of about 10 to about 30 wt % or about 12 to about 22 wt %; the third propylene-based elastomer in an amount based on the total blend of about 55 to about 75 wt % or about 60 to about 70 wt %; and the fourth propylene-based elastomer in an amount based on the total blend of about 1.0 to about 10 wt % or about 2.0 to about 7.0 wt %.

3. Third Blend

In various embodiments, a third blend comprising the second and fourth propylene-based elastomers as described herein is provided. The second propylene-based elastomer may be present in the first blend in an amount based on the total blend of at least about 75 wt %, at least about 80 wt %, at least about 85 wt %, at least about 90 wt %, at least about 95 wt %, or at least about 98 wt %. Additionally or alternatively, the second propylene-based elastomer may be present in the third blend in an amount based on the total blend of about 75 to about 98 wt %, about 80 to about 98 wt %, about 80 to about 95 wt %, or about 85 to about 95 wt %, particularly, about 80 to about 98 wt % or about 85 to about 95 wt %.

The fourth propylene-based elastomer may be present in the third blend in an amount based on the total blend of at least about 1.0 wt %, at least about 2.0 wt %, at least about 4.0 wt %, at least about 5.0 wt %, at least about 7.0 wt %, at least about 10 wt %, at least about 15 wt %, or at least about 20 wt %. Additionally or alternatively, the fourth propylene-based elastomer may be present in the third blend in an amount based on the total blend of about 1.0 to about 20 wt %, about 2.0 to about 20 wt %, about 2.0 to about 15 wt %, about 4.0 to about 15 wt %, about 5.0 to about 15 wt %, about 7.0 to about 15 wt %, or about 7.0 to about 10 wt %, particularly, about 2.0 to about 20 wt % or about 5.0 to about 15 wt %.

In a particular embodiment, a carpet backing layer is provided comprising a third blend as described herein. The third blend may comprise: the second propylene-based elastomer in an amount based on the total blend of about 80 to about 98 wt % or about 85 to 95 wt %; and the fourth propylene-based elastomer in an amount based on the total blend of about 2.0 to about 20 wt % or about 5.0 to 15 wt %.

Advantageously, the carpet backing layers described herein (e.g., comprising the first, second or third blend, have improved flexibility and improved clarity. Thus, the carpet backing layer may have a 1% secant flexural modulus, as measured according to ASTM D790, of less than about 300 MPa, less than about 275 MPa, less than about 250 MPa, less than about 225 MPa, less than about 200 MPa, less than about 175 MPa, less than about 150 MPa, less than about 125 MPa, less than about 100 MPa, less than about 75 MPa, less than about 50 MPa, less than about 30 MPa with a lower limit of about 20 MPa. Additionally or alternatively, the carpet backing layer may have a 1% secant flexural modulus, as measured according to ASTM D790, about 20 to about 300 MPa, about 20 to about 200 MPa, about 20 to about 100 MPa, or about 20 to about 75 MPa.

In a further embodiment, the carpet backing layer may have a Hf of about −50 to about −5.0 J/g, about −40 to about −10 J/g, about −35 to about −15 J/g, −33 to about −17 J/g, or about −31 J/g to about −19 J/g.

In another embodiment, the carpet backing layer may have a crystallization point ($T_c$), of greater than about 15° C., greater than about 20° C., greater than about 23° C., greater than about 25° C., greater than about 30° C., greater than about 35° C., greater than about 40° C., greater than about 45° C., greater than about 50° C., or greater than about 55° C. with an upper limit of about 65° C. or about 60° C. Additionally or alternatively, the carpet backing layer may have a crystallization point ($T_c$) of about 15° C. to about 65° C., about 20° C. to about 65° C., about 20° C. to about 60° C. or about 23° C. to about 60° C.

In a particular embodiment, the carpet backing layer described herein may have one or more of the following:
(i) a 1% secant flexural modulus of less than about 200 MPa or less than about 100 MPa;
(ii) a Hf of about −40 J/g to about −10 J/g or about −31 J/g to about −19 J/g; and/or
(iii) a $T_c$ of greater than about 20° C. or greater than about 23° C.

Additionally or alternatively, the carpet backing layer described herein may have two of (i), (ii) and (iii). For example, the carpet backing layer may have (i) and (ii), (i) and (iii), or (ii) and (iii). Alternatively, the carpet backing layer may have (i), (ii) and (iii).

In another embodiment, a carpet is provided herein. The carpet comprises a backing layer as described herein and plurality of fibers attached to the backing layer. The plurality of fibers may be comprised of any suitable material, such as, but not limited to, polypropylene, nylon, wool, cotton, acrylic, polyester, polyethylene terephthalate (PET) and combinations thereof. In particular, the plurality of fibers may be woven microfiber polyester, for example 3D woven microfiber polyester.

Additionally or alternatively, the carpet described herein may include a filler in the backing layer. The classes of materials described herein that are useful as fillers can be utilized alone or admixed to obtain desired properties. In any of the embodiments, the filler may be present at up to about 80 wt %, preferably up to about 70 wt %, more preferably from about 60 wt % to about 65 wt %, based on the total weight of the layers.

Desirable fillers can be organic fillers and/or inorganic fillers. Useful fillers include such materials as carbon black, fly ash, graphite, cellulose, starch, flour, wood flour, and polymeric fibers like polyester-based, polyamide-based materials, etc. Preferred examples of fillers are calcium carbonate, aluminum trihydrate, talc, glass fibers, marble dust, cement dust, clay, feldspar, silica or glass, fumed silica, alumina, magnesium oxide, antimony oxide, zinc oxide, barium sulfate, calcium sulfate, aluminum silicate, calcium silicate, titanium dioxide, titanates, clay, nanoclay, organo-modified clay or nanoclay, glass microspheres and chalk. In some embodiments, the one or more layers of the carpet comprise a filler for improving the flame retardant properties of the carpet, such as aluminum trihydrate or calcium carbonate.

III. Methods of Making the Carpet

Also provided are methods for making the carpet described herein. The method for making a carpet may comprise attaching a backing layer as described herein to a plurality fibers as described herein (e.g., polypropylene, nylon, linen, wool, cotton, acrylic, polyester, polyethylene terephthalate (PET), 3D woven microfiber polyester) to form the carpet.

Any conventional tufting or needle-punching apparatus and stitch patterns can be used with the plurality of fibers. Tufted yarn loops may be left uncut to produce a loop pile; cut to make cut pile; or cut, partially cut and uncut to make a face texture known as tip sheared. Tufted yarn may be digitigally printed using convention three-dimensional carpet printing techniques. In particular, yarn that is tufted or needle-punched to make carpet often has varying quantities of processing materials, most commonly oily or waxy chemicals, known as spin-finish chemicals, remaining thereon from the yarn manufacturing processes. It has been found to be preferable to remove or displace all or substantially all of these processing materials prior to attaching the backing layer.

The backing layer can be attached to the plurality of fibers by various methods, including, hot compression, extrusion coating and sheet lamination. In particular, a molten blend of propylene-based elastomers (e.g., the first blend, the second blend, the third blend) may be extruded through a die so as to make a sheet which is as wide as the carpet. The molten, extruded sheet may be applied to the plurality of fibers. Since the sheet is molten, the sheet will conform to the shape of the loops of yarn and further serve to fix the loops (e.g., plurality of fibers) in the backing layer.

Extrusion coating configurations include a monolayer T-type die, single-lip die coextrusion coating, dual-lip die coextrusion coating, and multiple stage extrusion coating.

Additionally or alternatively, a molten blend of propylene-based elastomers (e.g., the first blend, the second blend, the third blend) may be extruded through a die so as to make a sheet which is as wide as the carpet, which is then attached to the plurality of fibers via known hot compression techniques under suitable conditions. For example, suitable conditions can include a temperature of about 55° C. to about 75° C., about 60° C. to about 70° C. or about 65° C.; and a pressure of about 0.3 to about 1.3 MPa, about 0.5 to about 1.0 MPa or about 0.8 MPa. Advantageously, a shorter period of time is needed to attach the backing layers described herein to the plurality of fibers. For example, the period of time may be less than 20 minutes, less than 15 minutes, less than 10 minutes, less than 8 minutes, less than 5 minutes, less than 3 minutes or about 1 minute, preferably less than about 10 minutes or less than about 5 minutes. Additionally or alternatively, the period of time may be about 1 to about 20 minutes, about 1 to about 15 minutes, about 1 to about 10 minutes, about 1 to about 8 minutes, about 1 to about 5 minutes or about 1 to about 3 minutes.

Additionally or alternatively, the methods of preparing the carpets can further comprise blending the first propylene-based elastomer in an amount of about 30 wt % to about 50 wt % or about 35 wt % to about 45 wt % with the second propylene-based elastomer in an amount of about 5.0 wt % to about 20 wt % or about 5.0 wt % to about 5 wt %, the third propylene-based elastomer in an amount of about 35 wt % to about 60 wt % or about 40 wt % to about 55 wt %, and the fourth propylene-based elastomer in an amount of about 1.0 wt % to about 10 wt % or about 2.0 wt % to about 7.0 wt % to form the first blend, which can be formed into the backing layer, e.g., via extrusion.

Additionally or alternatively, the methods of preparing the carpets can further comprise blending the first propylene-based elastomer in an amount of about 5.0 wt % to about 20 wt % or about 8.0 wt % to about 18 wt % with the second propylene-based elastomer in an amount of about 10 wt % to about 30 wt % or about 12 wt % to about 22 wt %, the third propylene-based elastomer in an amount of about 55 wt % to about 75 wt % or about 60 wt % to about 70 wt %, and the fourth propylene-based elastomer in an amount of about 1.0 wt % to about 10 wt % or about 2.0 wt % to about 7.0 wt % to form the second blend, which can be formed into the backing layer, e.g., via extrusion.

Additionally or alternatively, the methods of preparing the carpets can further comprise blending the second propylene-based elastomer in an amount of about 80 wt % to about 98 wt % or about 85 wt % to about 95 wt % with the fourth propylene-based elastomer in an amount of about 2.0 wt % to about 20 wt % or about 5.0 wt % to about 15 wt % to form the third blend, which can be formed into the backing layer, e.g., via extrusion.

With regard to extruding the first, second or third blend to form the backing layer sheet, the line speed of the extrusion process will depend on factors such as the particular polymer being extruded, the exact equipment being used, and the weight of polymer being applied. The extrusion coating melt temperature principally depends on the particular polymer being extruded.

Since the backing layer may be relied on to encapsulate and lock the yarn (e.g., plurality of fibers) in place, this layer may have a MI high enough (melt viscosity low enough), for example, of from a lower limit of about 25 g/10 min or about 40 g/10 min to an upper limit of about 50 g/10 min, to promote encapsulation and locking of the yarn. Auxiliary equipment such as a pre-heater can be used in addition to a convection oven or infrared panels for heating the plurality of fibers.

The extruded polymer(s) can either be used neat, or can have one or more additive included. A preferred additive is an inorganic filler. Examples of such fillers include, but are not limited to, calcium carbonate, aluminum trihydrate, talc, and barite. Inorganic mineral fillers can improve yarn encapsulation and locking which in turn improves the performance of the tuft bind strength and tuft lock strength of extrusion coated carpet samples. Preferably, filler is added at a level of up to about 80 wt %, preferably up to about 70 wt %, more preferably from about 60 wt % to about 65 wt %, based on the total weight of the extruded layer. For the second layer of the present invention, fillers which may serve as flame retardant are preferred, such as aluminum trihydrate or calcium carbonate.

Other additives that may also be included include antioxidants such as sterically hindered phenols, sterically hindered amines and phospites may be used. Other possible additives include antiblock additives, pigments and colorants, anti-static agents, tackifiers (such as aromatic modified aliphatic hydrocarbon resins, e.g., those commercially available under the trade name ESCOREZ™ (ExxonMobil Chemical Company, Tex., USA)), compatibilizers (functionalized ethylene copolymers, preferably maleic anhydride functionalized elastomeric ethylene copolymers, e.g., those commercially available under the trade name EXXELOR™ (ExxonMobil Chemical Company, Tex., USA)), processing aids (such as stearic acid), antimicrobial agents (such as quaternary ammonium salts), chill roll release additives (such as fatty acid amides) and other aids (such as metallocene-based homopolymers, e.g., those commercially available under the trade name ACHIEVE™ (ExxonMobil Chemical Company, Tex., USA)).

The carpet construction and the methods described herein are particularly suited for making carpet tile. Carpet tile is typically made by producing a length of backed carpet and then cutting the carpet into the appropriate sized squares. The most common sizes include 18 inches (45.7 cm) square, 24 inches (about 61.0 cm) square, or 50 cm square.

In various embodiments, the carpet includes no more than 150 g/m$^2$ of latex, no more than 100 g/m$^2$ of latex, no more than 50 g/m$^2$ of latex, no more than 20 g/m$^2$ of latex, or 0.0 g/m$^2$ of latex.

The carpets described herein may have improved properties, including tuft bind strength and tuft lock strength, and reliable construction, by substantially locking face yarn in place with use of a propylene-based elastomer. The carpets having a backing layer with blend of propylene-based elastomers as described herein also has improved flexibility and good processability as well as improved aesthetics due to the transparent backing layer.

EXAMPLES

Example 1

Preparation of Polymer Blends

Polymer blends (reported in Table 2) were prepared by neat blending using the polymers described below in Table 1.

TABLE 1

| Polymer | Melt mass-flow rate (MFR) g/10 min, 230° C./2.16 kg ASTM D1238 | Ethylene content, wt % | Vicat softening temperature ° C. ASTM D 1525 | Flexural Modulas 1% secant, MPa (psi) ASTM D790 |
|---|---|---|---|---|
| Vistamaxx 3588FL | 8 | 4 | 103 | 393 (57,100) |
| Vistamaxx 3000 | 8 | 11 | 66 | 59 (8,610) |
| Vistamaxx 6102 | 3 | 16 | 52 | 12 (1,790) |
| Vistamax 8880 | ~25,000 | 6 | — | — |

Vistamaxx 3588FL, Vistamaxx 3000, Vistamaxx 6102 and Vistamax 8880 are all propylene-based copolymers commercially available from ExxonMobil Chemical Company.

Twelve different blends (Formulations 1-12) were prepared according to Table 2 below.

TABLE 2

|  | Vistamaxx 3588FL (wt %) | Vistamaxx 3000 (wt %) | Vistamaxx 6102 (wt %) | Vistamaxx 8880 (wt %) |
|---|---|---|---|---|
| Formulation #1 | 100 | 0 | 0 | 0 |
| Formulation #2 | 90 | 0 | 0 | 10 |
| Formulation #3 | 0 | 100 | 0 | 0 |
| Formulation #4 | 0 | 90 | 0 | 10 |
| Formulation #5 | 0 | 0 | 100 | 0 |
| Formulation #6 | 0 | 0 | 90 | 10 |
| Formulation #7 | 24 | 40 | 31 | 5 |
| Formulation #8 | 39 | 9 | 47 | 5 |
| Formulation #9 | 63 | 18 | 14 | 5 |
| Formulation #10 | 31 | 57 | 7 | 5 |
| Formulation #11 | 9 | 69 | 17 | 5 |
| Formulation #12 | 13 | 17 | 65 | 5 |

Example 2

Differential Scanning Calorimetry and Flexural Modulus Testing of Polymer Blends (Formulations 1-12)

Differential Scanning Calorimetry (DSC) and Flexural Modulus tests were performed on each of Formulations 1-12. DSC testing was performed according to ASTM D3418 using a 10° C./min heating rate and Flexural Modulus testing was based on ASTM D790. The results are shown below in Table 3.

TABLE 3

| Formulation # | Flexural Modulus (MPa) | $T_c$ (° C.) | Hf (J/g) | $T_m$ (° C.) |
|---|---|---|---|---|
| 1 | 396 | 65 | −48 | 109 |
| 2 | 366 | 68 | −49 | 108 |
| 3 | 40 | 13 | −13 | 63 |
| 4 | 44 | 24 | −25 | 69 |
| 5 | 9 | Not Detectable | Not Detectable | 105 |
| 6 | 13 | 26 | −14 | Not Detectable |
| 7 | 55 | 43 | −27 | 90 |
| 8 | 60 | 56 | −31 | 105 |
| 9 | 158 | 59 | −39 | 104 |
| 10 | 85 | 54 | −35 | 96 |
| 11 | 40 | 31 | −26 | 100 |
| 12 | 25 | 34 | −19 | 99 |

The DSC test results demonstrated that the addition of Vistamaxx 8880 increased the $T_c$ of compounds by 3° C. and 11° C., respectively, when blending with Vistamaxx 3588 and 3000. For pure Vistamaxx 6102, the crystallization was to slow to be detected but blending it with Vistamaxx 8880 aided in crystallization resulting in a $T_c$ of 26° C. The Flexural Modulus of Formulations #1 and #2 were too stiff, for example, for applications requiring a Flexural Modulus of below 200 MPa, while the other formulations had varying flexibility which can be used for different carpet products such as wall-to-wall carpeting, tapestry, door mats, etc.

Based on the data in Table 3, predictive models were built using the software Design Expert® as follows:

Predict Flexural Modulus=−22−148*((Vistamaxx 6102%−0.5)/0.5)−88*((Vistamaxx 3000%−0.5)/0.5)+((Vistamaxx 6102%−0.5)/0.5)*(((Vistamaxx 3000%−0.5)/0.5)*21)−68*((Vistamaxx 3588%−0.5)/0.5)+((Vistamaxx 6102%−0.5)/0.5)*(((Vistamaxx 3588%−0.5)/0.5)*(−137))+((Vistamaxx 3000%−0.5)/0.5)*(((Vistamaxx 3588%—0.5)/0.5)*(−92))

Predict ΔH=16+57*((Vistamaxx 6102%−0.5)/0.5)+48*((Vistamaxx 3000%−0.5)/0.5)+((Vistamaxx 6102%−0.5)/0.5)*(((Vistamaxx 3000%−0.5)/0.5)*21)+36*((Vistamaxx 3588%−0.5)/0.5)+((Vistamaxx 6102%−0.5)/0.5)*(((Vistamaxx 3588%−0.5)/0.5)*24)+((Vistamaxx 3000%−0.5)/0.5)*(((Vistamaxx 3588%−0.5)/0.5)*20)+((Vistamaxx 6102%−0.5)/0.5)*(((Vistamaxx 3000%−0.5)/0.5)*(((Vistamaxx 3588%−0.5)/0.5)*30))

Figure 1:
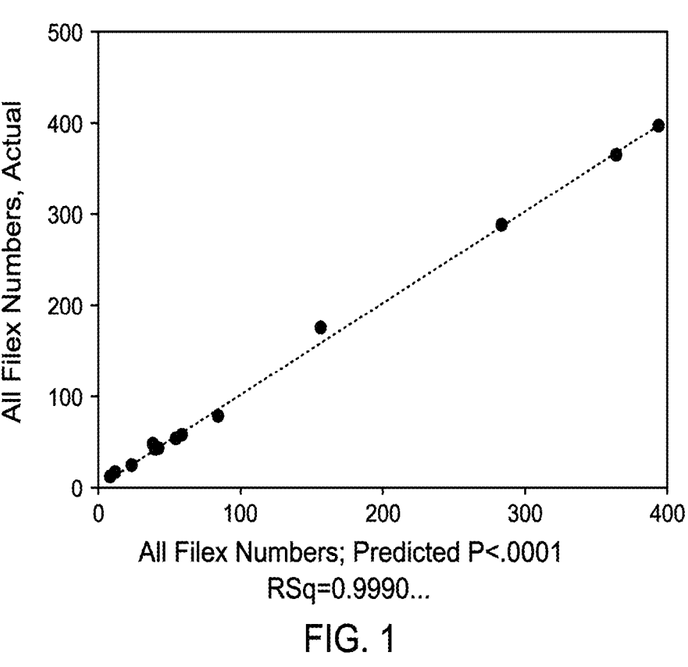
FIG. 1 illustrates flexural modulus predictions and test results for Formulations 1-12.
Figure 2:
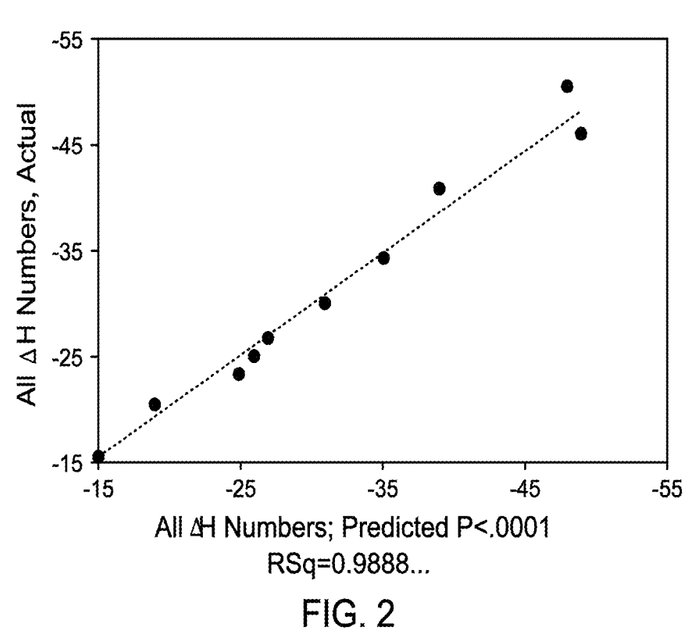
FIG. 2 illustrates Hf predictions and test results for Formulations 1-12.

The predictive models compared to the test results are shown in FIGS. 1 and 2.

Example 3

Processability of Trial Formulations

Based on the test results and predictive models in Example 2, Trial Formulations 1-8 were selected according to Table 4 below.

TABLE 4

| Vistamaxx Grade | 3588 (%) | 3000 (%) | 6102 (%) | 8880 (%) | Test Flexural Modulus (MPa) | Test Hf (J/g) | Test $T_c$ (° C.) |
|---|---|---|---|---|---|---|---|
| Trial #1 (corresponds to Formulation #1) | 100 | 0 | 0 | 0 | 396 | −48 | 65 |
| Trial #2 (corresponds to Formulation #3) | 0 | 100 | 0 | 0 | 40 | −13 | 13 |
| Trial #3 (corresponds to Formulation #5) | 0 | 0 | 100 | 0 | 9 | Not Detectable | Not Detectable |
| Trial #4 (corresponds to Formulation #2) | 90 | 0 | 0 | 10 | 366 | −49 | 68 |
| Trial #5 (corresponds to Formulation #4) | 0 | 90 | 0 | 10 | 44 | −25 | 24 |
| Trial #6 (corresponds to Formulation #6) | 0 | 0 | 90 | 10 | 13 | −14 | 26 |
| Trial #7 (corresponds to Formulation #8) | 39 | 9 | 47 | 5 | 60 | −31 | 56 |
| Trial #8 (corresponds to Formulation #12) | 13 | 17 | 65 | 5 | 25 | −19 | 34 |

The Trial Formulations 1-8 were processed with a 1-layer extrusion line from Mingfa Machinery. The machine had a die width of 1.5 m, a screw L/D of 30 and a cooling system consisting of 3 cooling rolls with room temperature water. The extruder temperature profile and die temperature profile are shown below in Tables 5 and 6, respectively.

TABLE 5

| | Extruder | | | | | | | | |
|---|---|---|---|---|---|---|---|---|---|
| | 1 | 2 | 3 | 4 | 5 | 6 | 7 | 8 | 9 |
| T (° C.) | 130 | 142 | 148 | 155 | 153 | 156 | 161 | 168 | 168 |

TABLE 6

| | Die Zone | | | | |
|---|---|---|---|---|---|
| | 1 | 2 | 3 | 4 | 5 |
| T (° C.) | 150 | 145 | 145 | 145 | 150 |

Figure 3A:
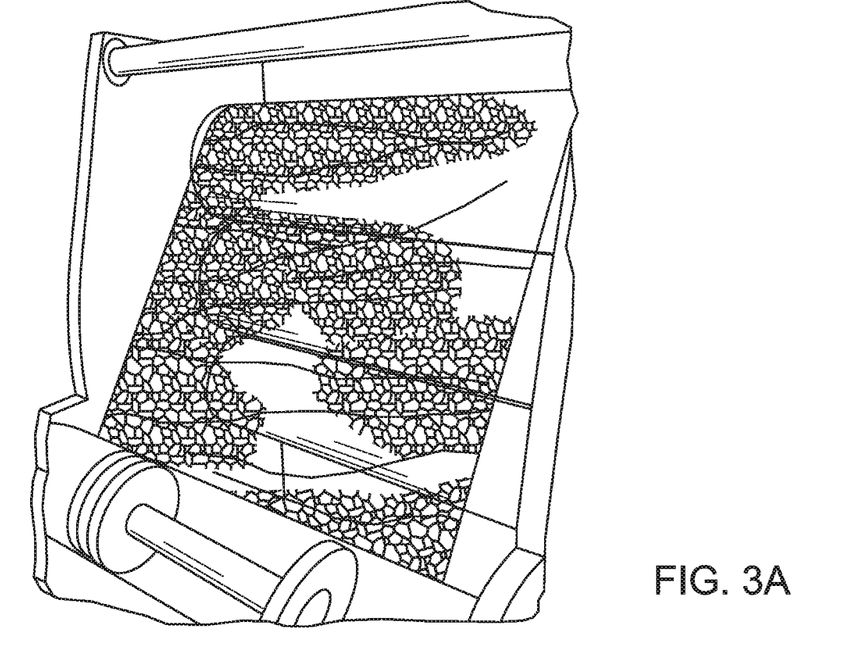
FIG. 3a is a photograph illustrating poor processability of Trial Formulation #1, 2, 3, 6, and 8.
Figure 3B:
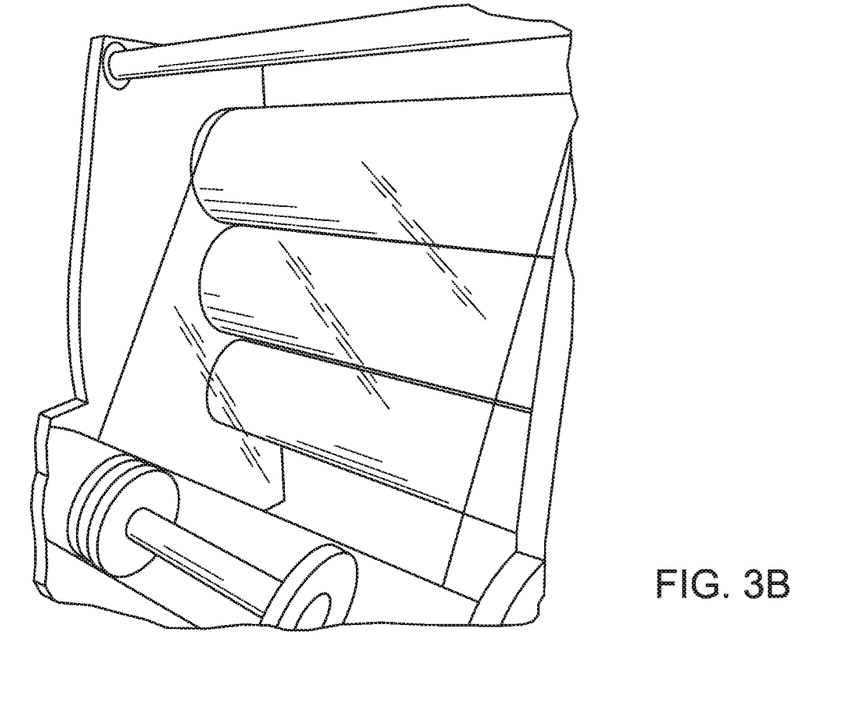
FIG. 3b is a photograph illustrating good processability of Trial Formulation #5 and 7.

It was determined that Trial Formulations 5, 7 and 8 all had good processability and Trial Formulations 1, 2, 3, 4 and 6 all had poor processability. Processability was evaluated at 1.5 m/min line speed. Examples of poor processability and good processability are shown in FIGS. 3a and 3b, respectively.

All documents described herein are incorporated by reference herein, including any priority documents and/or testing procedures to the extent they are not inconsistent with this text. As is apparent from the foregoing general description and the specific embodiments, while forms of the invention have been illustrated and described, various modifications can be made without departing from the spirit and scope of the invention. Accordingly, it is not intended that the invention be limited thereby. Likewise, the term "comprising" is considered synonymous with the term "including." Likewise, whenever a composition, an element or a group of elements is preceded with the transitional phrase "comprising," it is understood that we also contemplate the same composition or group of elements with transitional phrases "consisting essentially of," "consisting of," "selected from the group of consisting of," or "is" preceding the recitation of the composition, element, or elements, and vice versa.

What is claimed is:

1. A carpet backing layer comprising one of the following:
   (i) a first blend comprising:
      (A) about 30 wt % to about 50 wt % of a first propylene-based elastomer comprising at least about 90 wt % propylene-derived units and about 2 to about 10 wt % ethylene-derived units, by weight of the propylene-based elastomer, wherein the first propylene-based elastomer has a 1% secant flexural modulus of about 350 MPa to about 450 MPa;
      (B) about 5 wt % to about 20 wt % of a second propylene-based elastomer comprising at least about 80 wt % propylene-derived units and about 5 to about 20 wt % ethylene-derived units, by weight of the propylene-based elastomer, wherein the second propylene-based elastomer has a 1% secant flexural modulus of about 40 MPa to about 70 MPa;
      (C) about 35 wt % to about 60 wt % of a third propylene-based elastomer comprising at least about 75 wt % propylene-derived units and about 10 to about 25 wt % ethylene-derived units, by weight of the propylene-based elastomer, wherein the third propylene-based elastomer has a 1% secant flexural modulus of about 5.0 MPa to about 20 MPa; and
      (D) about 1 wt % to about 10 wt % of a fourth propylene-based elastomer comprising at least about 90 wt % propylene-derived units and about 2 to about 10 wt % ethylene-derived units, by weight of the propylene-based elastomer, wherein the fourth propylene-based elastomer has a melt mass-flow rate of at least about 20,000 g/10 min;
   (ii) a second blend comprising about 5 wt % to about 20 wt % of the first propylene-based elastomer; about 10 wt % to about 30 wt % of the second propylene-based elastomer; about 55 wt % to about 75 wt % of the third propylene-based elastomer; and about 1 wt % to about 10 wt % of the fourth propylene-based elastomer; or
(iii) a third blend comprising about 80 wt % to about 98 wt % of the second propylene-based elastomer present and about 2 wt % to about 20 wt % of the fourth propylene-based elastomer.

2. The carpet backing layer of claim 1, wherein the first blend comprises about 35 wt % to about 45 wt % of the first propylene-based elastomer; about 5 wt % to about 15 wt % of the second propylene-based elastomer; about 40 wt % to about 55 wt % of the third propylene-based elastomer; and about 2 wt % to about 7 wt % of the fourth propylene-based elastomer.

3. The carpet backing layer of claim 1, wherein the second blend comprises about 8 wt % to about 18 wt % of the first propylene-based elastomer; about 12 wt % to about 22 wt % of the second propylene-based elastomer; about 60 wt % to about 70 wt % of the third propylene-based elastomer; and about 2 wt % to about 7 wt % of the fourth propylene-based elastomer.

4. The carpet backing layer of claim 1, wherein the third blend comprises about 85 wt % to about 95 wt % of the second propylene-based elastomer and about 5 wt % to about 15 wt % of the fourth propylene-based elastomer.

5. The carpet backing layer of claim 1, wherein the carpet backing layer has one or more of the following:
(i) a 1% secant flexural modulus of less than about 200 MPa;
(ii) a Hf of about −40 J/g to about −10 J/g; and
(iii) a $T_c$ of greater than about 20° C.

6. The carpet backing layer of claim 5, wherein the carpet backing layer has two or more of the following:
(i) a 1% secant flexural modulus of less than about 200 MPa;
(ii) a Hf of about −40 J/g to about −10 J/g; and
(iii) a $T_c$ of greater than about 20° C.

7. The carpet backing layer of claim 5, wherein the carpet backing layer has
(i) a 1% secant flexural modulus of less than about 200 MPa;
(ii) a Hf of about −40 J/g to about −10 J/g; and
(iii) a $T_c$ of greater than about 20° C.

8. The carpet backing layer of claim 1, wherein the carpet backing layer has one or more of the following:
(i) a 1% secant flexural modulus of less than about 100 MPa;
(ii) a Hf of about −31 J/g to about −19 J/g; and
(iii) a $T_c$ of greater than about 23° C.

9. A carpet comprising:
a backing layer comprising one of the following:
(i) a first blend comprising:
(A) about 30 wt % to about 50 wt % of a first propylene-based elastomer comprising at least about 90 wt % propylene-derived units and about 2 to about 10 wt % ethylene-derived units, by weight of the propylene-based elastomer, wherein the first propylene-based elastomer has a 1% secant flexural modulus of about 350 MPa to about 450 MPa;
(B) about 5 wt % to about 20 wt % of a second propylene-based elastomer comprising at least about 80 wt % propylene-derived units and about 5 to about 20 wt % ethylene-derived units, by weight of the propylene-based elastomer, wherein the second propylene-based elastomer has a 1% secant flexural modulus of about 40 MPa to about 70 MPa;
(C) about 35 wt % to about 60 wt % of a third propylene-based elastomer comprising at least about 75 wt % propylene-derived units and about 10 to about 25 wt % ethylene-derived units, by weight of the propylene-based elastomer, wherein the third propylene-based elastomer has a 1% secant flexural modulus of about 5.0 MPa to about 20 MPa; and
(D) about 1 wt % to about 10 wt % of a fourth propylene-based elastomer comprising at least about 90 wt % propylene-derived units and about 2 to about 10 wt % ethylene-derived units, by weight of the propylene-based elastomer, wherein the fourth propylene-based elastomer has a melt mass-flow rate of at least about 20,000 g/10 min;
(ii) a second blend comprising about 5 wt % to about 20 wt % of the first propylene-based elastomer; about 10 wt % to about 30 wt % of the second propylene-based elastomer; about 55 wt % to about 75 wt % of the third propylene-based elastomer; and about 1 wt % to about 10 wt % of the fourth propylene-based elastomer; or
(iii) a third blend comprising about 80 wt % to about 98 wt % of the second propylene-based elastomer and about 2 wt % to about 20 wt % of the fourth propylene-based elastomer; and
a plurality of fibers attached to the backing layer.

10. The carpet of claim 9, wherein the first blend comprises about 35 wt % to about 45 wt % of the first propylene-based elastomer; about 5 wt % to about 15 wt % of the second propylene-based elastomer present; about 40 wt % to about 55 wt % of the third propylene-based elastomer; and about 2 wt % to about 7 wt % of the fourth propylene-based elastomer.

11. The carpet of claim 9, wherein the second blend comprises about 8 wt % to about 18 wt % of the first propylene-based elastomer; about 12 wt % to about 22 wt % of the second propylene-based elastomer; about 60 wt % to about 70 wt % of the third propylene-based elastomer; and about 2 wt % to about 7 wt % of the fourth propylene-based elastomer.

12. The carpet of claim 9, wherein the third blend comprises about 85 wt % to about 95 wt % of the second propylene-based elastomer and about 5 wt % to about 15 wt % of the fourth propylene-based elastomer.

13. The carpet of claim 9, wherein the backing layer has one or more of the following:
(i) a 1% secant flexural modulus of less than about 200 MPa;
(ii) a Hf of about −40 J/g to about −10 J/g; and
(iii) a $T_c$ of greater than about 20° C.

14. The carpet of claim 9, wherein the backing layer has two or more of the following:
(i) a 1% secant flexural modulus of less than about 200 MPa;
(ii) a Hf of about −40 J/g to about −10 J/g; and
(iii) a $T_c$ of greater than about 20° C.

15. The carpet of claim 9, wherein the backing layer has one or more of the following:
(i) a 1% secant flexural modulus of less than about 100 MPa;
(ii) a Hf of about −31 J/g to about −19 J/g; and
(iii) a $T_c$ of greater than about 23° C.

16. The carpet of claim 9, wherein the fibers comprise at least one of polypropylene, nylon, wool, cotton, acrylic, polyester, and polyethylene terephthalate.

17. A method for making a carpet comprising:
attaching a backing layer to a plurality of fibers via hot compression for a period of time of less than about 10 minutes to form the carpet;
wherein the backing layer comprises one of the following:
  (i) a first blend comprising:
    (A) about 30 wt % to about 50 wt % of a first propylene-based elastomer comprising at least about 90 wt % propylene-derived units and about 2 to about 10 wt % ethylene-derived units, by weight of the propylene-based elastomer, wherein the first propylene-based elastomer has a 1% secant flexural modulus of about 350 MPa to about 450 MPa;
    (B) about 5 wt % to about 20 wt % of a second propylene-based elastomer comprising at least about 80 wt % propylene-derived units and about 5 to about 20 wt % ethylene-derived units, by weight of the propylene-based elastomer, wherein the second propylene-based elastomer has a 1% secant flexural modulus of about 40 MPa to about 70 MPa;
    (C) about 35 wt % to about 60 wt % of a third propylene-based elastomer comprising at least about 75 wt % propylene-derived units and about 10 to about 25 wt % ethylene-derived units, by weight of the propylene-based elastomer, wherein the third propylene-based elastomer has a 1% secant flexural modulus of about 5.0 MPa to about 20 MPa; and
    (D) about 1 wt % to about 10 wt % of a fourth propylene-based elastomer comprising at least about 90 wt % propylene-derived units and about 2 to about 10 wt % ethylene-derived units, by weight of the propylene-based elastomer, wherein the fourth propylene-based elastomer has a melt mass-flow rate of at least about 20,000 g/10 min;
  (ii) a second blend comprising about 5 wt % to about 20 wt % of the first propylene-based elastomer; about 10 wt % to about 30 wt % of the second propylene-based elastomer; about 55 wt % to about 75 wt % of the third propylene-based elastomer; and about 1 wt % to about 10 wt % of the fourth propylene-based elastomer; or
  (iii) a third blend comprising about 80 wt % to about 98 wt % of the second propylene-based elastomer and about 2 wt % to about 20 wt % of the fourth propylene-based elastomer.

18. The method of claim 17, wherein the backing layer is attached to the plurality of fibers at a temperature of about 60° C. to about 70° C. and a pressure of about 0.5 to about 1.0 MPa.

19. The method of claim 17, wherein the backing layer is attached to the plurality of fibers for a period of time of less than about 5 minutes to form the carpet.

20. The method of claim 17, wherein the first blend comprises about 35 wt % to about 45 wt % of the first propylene-based elastomer; about 5 wt % to about 15 wt % of the second propylene-based elastomer; about 40 wt % to about 55 wt % of the third propylene-based elastomer; and about 2 wt % to about 7 wt % of the fourth propylene-based elastomer.

21. The method of claim 17, wherein the second blend comprises about 8 wt % to about 18 wt % of the first propylene-based elastomer; about 12 wt % to about 22 wt % of the second propylene-based elastomer; about 60 wt % to about 70 wt % of the third propylene-based elastomer present; and about 2 wt % to about 7 wt % of the fourth propylene-based elastomer.

22. The method of claim 17, wherein the third blend comprises about 85 wt % to about 95 wt % of the second propylene-based elastomer and about 5 wt % to about 15 wt % of the fourth propylene-based elastomer.

23. The method of claim 17, wherein the backing layer has one or more of the following:
  (i) a 1% secant flexural modulus of less than about 200 MPa;
  (ii) a Hf of about −40 J/g to about −10 J/g; and
  (iii) a $T_c$ of greater than about 20° C.

24. The method of claim 17, wherein the backing layer has one or more of the following:
  (iv) a 1% secant flexural modulus of less than about 100 MPa;
  (v) a Hf of about −31 J/g to about −19 J/g; and
  (vi) a $T_c$ of greater than about 23° C.

25. The method of claim 17, wherein the fibers comprise at least one of polypropylene, nylon, wool, cotton, acrylic, polyester, and polyethylene terephthalate.

* * * * *